United States Patent [19]

Hemmi et al.

[11] Patent Number: 5,057,513

[45] Date of Patent: Oct. 15, 1991

[54] SPIRO-THIAZEPINE DERIVATIVES USEFUL AS PAF ANTAGONISTS

[75] Inventors: Keiji Hemmi, Tsukuba; Ichiro Shima, Moriyamachi; Naoki Fukami, Ibaraki; Masashi Hashimoto, Tsukuba, all of Japan

[73] Assignee: Fujisawa Pharmaceutical Co., Ltd., Osaka, Japan

[21] Appl. No.: 518,951

[22] Filed: May 4, 1990

[30] Foreign Application Priority Data

May 25, 1989 [GB] United Kingdom ................ 8912055
Sep. 18, 1989 [GB] United Kingdom ................ 8921077
Nov. 10, 1989 [GB] United Kingdom ................ 8925403

[51] Int. Cl.$^5$ ................ C07D 513/02; C07D 281/10; A61K 31/55
[52] U.S. Cl. ................ 514/211; 540/488; 540/491
[58] Field of Search ................ 540/488, 491; 514/211

[56] References Cited

U.S. PATENT DOCUMENTS 3,639,666  2/1972  Narayanan ................ 540/543
3,907,800  9/1975  Etienne et al. ................ 546/218

FOREIGN PATENT DOCUMENTS 0026000  5/1983  European Pat. Off. .
0182273  5/1986  European Pat. Off. .
2340122  2/1974  Fed. Rep. of Germany .
2623192  5/1989  France .

OTHER PUBLICATIONS

Narayanan, V., Chemical Abstracts vol. 73, No. 120696k (1970).
Narayanan, V., Chemical Abstracts vol. 77, No. 56415w (1972).

*Primary Examiner*—Mukund J. Shah
*Assistant Examiner*—Philip Datlow
*Attorney, Agent, or Firm*—Oblon, Spivak, McClelland, Maier & Neustadt

[57] ABSTRACT

The invention relates to thiazepine derivatives, which are antagonists of platelet activating factor, of the formula:

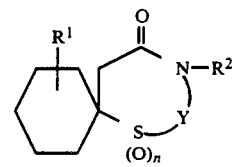

wherein $R^1$ is ar(lower)alkyl which may have suitable substituent(s), $R^2$ is hydrogen, lower alkyl which may have suitable substituent(s), or a group of the formula:

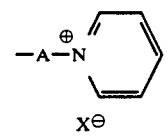

in which A is lower alkylene and X is halogen, n is 0, 1 or 2 and Y is —CH$_2$—CH$_2$— or

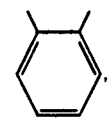

or a pharmaceutically acceptable salt thereof.

10 Claims, No Drawings

SPIRO-THIAZEPINE DERIVATIVES USEFUL AS PAF ANTAGONISTS

This invention relates to new thiazepine derivatives. More particularly, it relates to new thiazepine derivatives and pharmaceutically acceptable salt thereof which are antagonists of platelet activating factor (hereinafter referred to as "PAF"), to processes for preparation thereof and to a pharmaceutical composition comprising the same.

The thiazepine derivatives of this invention can be represented by the following formula (I):

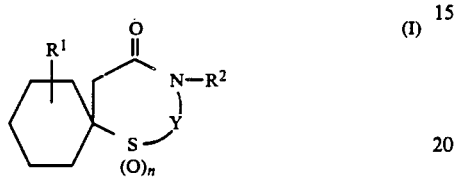
(I)

wherein
$R^1$ is ar(lower)alkyl which may have suitable substituent(s),
$R^2$ is hydrogen, lower alkyl which may have suitable substituent(s), or a group of the formula:

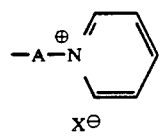

(in which A is lower alkylene and X is halogen),
n is 0, 1 or 2 and
Y is —CH$_2$—CH$_2$— or

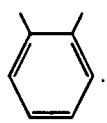

According to the present invention, the new thiazepine derivatives (I) can be prepared by the processes which are illustrated in the following scheme.

Process 1

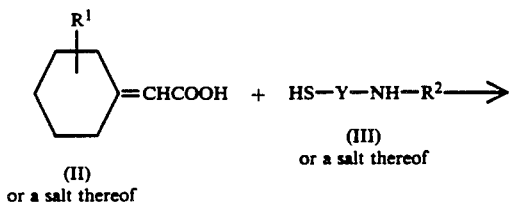

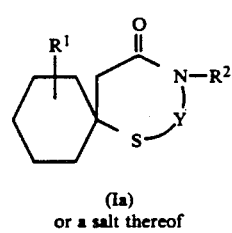
(Ia)
or a salt thereof

Process 2

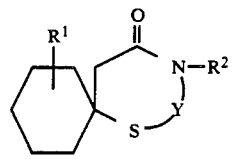
(Ia)
or a salt thereof

↓

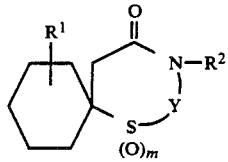
(Ib)
or a salt thereof

Process 3

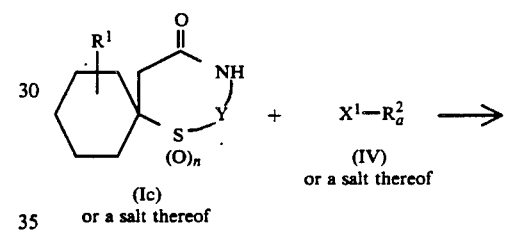
(Ic)
or a salt thereof

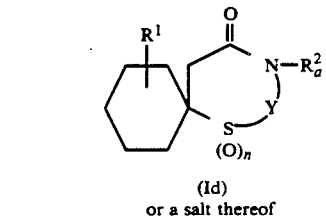
(Id)
or a salt thereof

Process 4

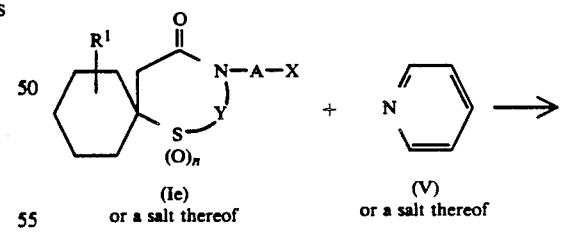
(Ie)
or a salt thereof (V)
or a salt thereof

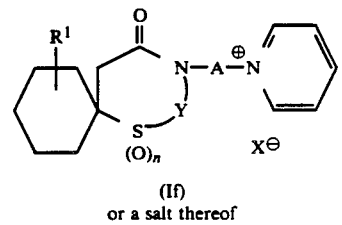
(If)
or a salt thereof wherein
$R^1$, $R^2$, n, Y, A and X are each as defined above,
m is 1 or 2, $R_a^2$ is lower alkyl which may have suitable substituent(s), and $X^1$ is halogen.

The compound (II) can be prepared by the processes which are illustrated in the following scheme.

Process A

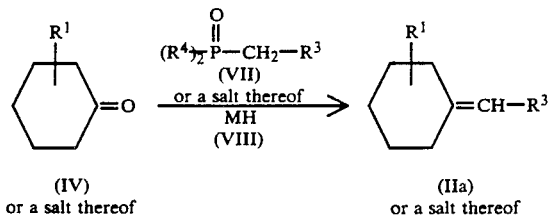

(IV) or a salt thereof (IIa) or a salt thereof

Process B

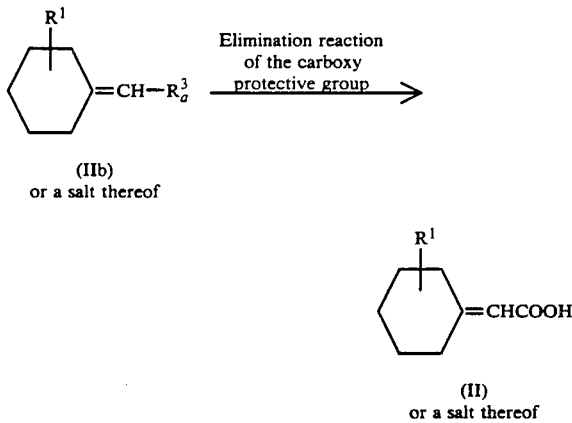

(IIb) or a salt thereof (II) or a salt thereof wherein
$R^1$ is as defined above,
M is an alkali metal,
$R^3$ is carboxy or protected carboxy,
$R^4$ is lower alkoxy and
$R_a^3$ is protected carboxy.

The compound (VI) can be prepared according to the methods disclosed in the following Preparations 2(1) and 2(2) or similar methods thereto.

Suitable pharmaceutically acceptable salts of the object compound (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, trifluoroacetate, etc.), an inorganic acid salt (e.g. hydrochloride, hydrobromide, sulfate, phosphate, etc.), a salt with an amino acid (e.g. arginine, aspartic acid, glutamic acid, lysine, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "lower alkyl" and "lower alkyl moiety" in the term "ar(lower)alkyl" may include straight or branched one having 1 to 6 carbon atom(s), such as methyl, ethyl, propyl, isopropyl, butyl, isobutyl, sec-butyl, t-butyl, pentyl, t-pentyl, hexyl or the like.

Suitable "substituent" in the term "ar(lower)alkyl which may have suitable substituent(s)" may include halogen (e.g., chlorine, bromine, fluorine and iodine), lower alkoxy (e.g., methoxy, ethoxy, propoxy, isopropoxy, butoxy, isobutoxy, t-butoxy, pentyloxy, t-pentyloxy, hexyloxy, etc.), lower alkyl (e.g., methyl, ethyl, propyl, isopropyl, butyl, isobutyl, sec-butyl, t-butyl, pentyl, t-pentyl, hexyl, etc.) and the like.

Suitable "aryl moiety" in the term "ar(lower)alkyl" may include phenyl, naphthyl and the like.

Suitable "substituent" in the term "lower alkyl which may have suitable substituent(s)" may include di(lower)alkylamino (e.g., dimethylamino, diethylamino, diisopropylamino, dipropylamino, dibutylamino, di(t-butyl)amino, dipentylamino, dihexylamino, etc.); heterocyclic group which may have suitable substituent(s); halogen; and the like.

Suitable "heterocyclic group" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6 membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.; saturated 3 to 6-membered heteromonocyclic group containing 1 to 4 nitrogen atoms (e.g., pyrrolidinyl, imidazolidinyl, piperidino, piperazinyl, etc.); unsaturated condensed heterocyclic group containing 1 to 5 nitrogen atoms for example, indolyl, isoindolyl, indolizinyl, benzimidazolyl, quinolyl, isoquinolyl, quinoxalinyl, naphthyridinyl, phthalazinyl, indazolyl, benzotriazolyl, tetrazolopyridazinyl (e.g., tetrazolo[1,5-b]pyridazinyl, etc.), etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g. 1,2,4-oxadiazolyl, 1,3,4-oxadiazolyl, 1,2,5-oxadiazolyl, etc.), etc.; saturated 3 to 6-membered heteromonocyclic group containing 1 to 2 oxygen atoms and 1 to 3 nitrogen atoms (e.g., morpholinyl, etc.); unsaturated condensed heterocyclic group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.), etc.; saturated 3 to 6-membered heteromonocyclic group containing 1 to 2 sulfur atoms and 1 to 3 nitrogen atoms (e.g., thiazolidinyl, etc.); unsaturated condensed heterocyclic group containing 1 to 2 sulfur atoms and 1 to 3 nitrogen atoms (e.g., benzothiazolyl, benzothiadiazolyl, etc.) and the like, and the said heterocyclic group may have suitable substituent(s) such as halogen (e.g., chlorine, bromine, fluorine and iodine), lower alkoxy (e.g., methoxy, ethoxy, propoxy, isopropoxy, butoxy, isobutoxy, t-butoxy, pentyloxy, t-pentyloxy, hexyloxy, etc.), lower alkyl (e.g., methyl, ethyl, propyl, isopropyl, butyl, isobutyl, sec-butyl, t-butyl, pentyl, t-pentyl, hexyl, etc.) or the like.

Suitable "halogen" may include chlorine, bromine, fluorine and iodine.

Suitable "lower alkylene" may include methylene, ethylene, trimethylene, tetramethylene, pentamethylene, hexamethylene and the like.

Suitable "protected carboxy" may include esterified carboxy and the like. And suitable examples of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.); lower alkenyl ester (e.g., vinyl ester, allyl ester, etc.); lower alkynyl ester (e.g., ethynyl ester, propynyl ester, etc.); lower alkoxyalkyl ester (e.g., methoxymethyl ester, ethoxymethyl ester, isopropoxymethyl ester, 1-methoxyethyl ester, 1-ethoxyethyl ester, etc.); lower alkylthioalkyl ester (e.g., methylthiomethyl ester, ethylthiomethyl ester, ethylthioethyl ester, isopropylthiomethyl ester, etc.); mono(or di or tri)-halo(lower)alkyl ester (e.g. 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.); lower alkanesulfonyl(lower)alkyl ester (e.g, mesylmethyl ester, 2-mesylethyl ester etc.); ar(lower)alkyl ester, for example, phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have one or more suitable substituent(s) such as substituted or unsubstituted phenyl ester (e.g. phenyl ester, tolyl ester, t-butylphenyl ester, xylyl ester, mesityl ester, cumenyl ester, 4-chlorophenyl ester, 4-methoxyphenyl ester, etc.); tri(lower)alkyl silyl ester; lower alkylthioester (e.g. methylthioester, ethylthioester, etc.) and the like.

Suitable "lower alkoxy" may include methoxy, ethoxy, propoxy, isopropoxy, butoxy, isobutoxy, t-butoxy, pentyloxy, t-pentyloxy, hexyloxy and the like.

Suitable "alkali metal" may include sodium, potassium and the like.

The preferred embodiments of the object compound (I) are as follows.

$R^1$ is ar(lower)alkyl (more preferably ar($C_1$-$C_3$)alkyl) which may have one to three (more preferably one or two) substituent(s), in which the aryl moiety is selected from the group consisting of phenyl and naphthyl and the substituent is selected from the group consisting of halogen, lower alkoxy (more preferably $C_1$-$C_3$ alkoxy) and lower alkoxy (more preferably $C_1$-$C_3$ alkyl).

$R^2$ is hydrogen; lower alkyl (more preferably $C_1$-$C_4$ alkyl) which may have one to three (more preferably one or two) substituent(s) selected from the group consisting of di(lower)alkylamino (more preferably di($C_1$-$C_3$)alkylamino), halogen and heterocyclic group (more preferably pyridyl, morpholinyl, thiazolyl, quinolyl or quinoxalinyl), in which the heterocyclic group may have one to three (more preferably one or two) substituent(s) selected from the group consisting of halogen, lower alkoxy (more preferably $C_1$-$C_3$ alkoxy) and lower alkyl (more preferably $C_1$-$C_3$ alkyl); or a group of the formula:

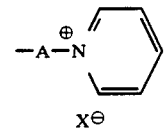

[in which A is lower alkylene (more preferably $C_1$-$C_4$ alkylene) and X is halogen].

n is 0, 1 or 2.

Y is —$CH_2CH_2$— or

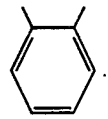

The processes for preparing the object compound of the present invention are explained in detail in the following.

Process 1

The compound (Ia) or a salt thereof can be prepared by reacting the compound (II) or a salt thereof with the compound (III) or a salt thereof.

Suitable salts of the compounds (Ia), (II) and (III) can be referred to the ones as exemplified for the compound (I).

This reaction is usually carried out in a solvent such as benzene, N,N-dimethylformamide, tetrahydrofuran, diethyl ether or any other solvent which does not adversely affect the reaction.

The reaction temperature is not critical and the reaction is usually carried out under warming or under heating.

Process 2

The compound (Ib) or a salt thereof can be prepared by subjecting the compound (Ia) or a salt thereof to oxidation reaction.

Suitable salts of the compound (Ib) can be referred to the ones as exemplified for the compound (I).

The present oxidation reaction can be carried out by a conventional method, for example by using an oxidizing agent such as m-chloroperbenzoic acid, perbenzoic acid, peracetic acid or the like.

This reaction is usually carried out in a solvent such as benzene, N,N-dimethylformamide, tetrahydrofuran, methylene chloride, diethyl ether or any other solvent which does not adversely affect the reaction.

The reaction temperature is not critical and the reaction is usually carried out under cooling or at ambient temperature.

Process 3

The compound (Id) or a salt thereof can be prepared by reacting the compound (Ic) or a salt thereof with the compound (IV) or a salt thereof.

Suitable salts of the compounds (Ic), (Id) and (IV) can be referred to the ones as exemplified for the compound (I).

This reaction is usually carried out in the presence of base.

Suitable base may include an inorganic base such as alkali metal hydride (e.g. sodium hydride, etc.), alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.) picoline, N-methylpyrrolidine, N-methylmorpholine or the like.

This reaction is usually carried out in a solvent such as benzene, N,N-dimethylformamide, tetrahydrofuran, diethyl ether, dimethylsulfoxide or any other solvent which does not adversely affect the reaction.

The reaction temperature is not critical and the reaction is usually carried out at ambient temperature, under warming or under heating.

Process 4

The compound (If) or a salt thereof can be prepared by reacting the compound (Ie) or a salt thereof with the compound (V) or a salt thereof.

The reaction temperature is not critical and the reaction is usually carried out under warming to heating.

The processes for preparing the starting compound of the present invention are explained in detail in the following.

Process A

The compound (IIa) or a salt thereof can be prepared by reacting the compound (VI) or a salt thereof with a mixture of the compound (VII) or a salt thereof and the compound (VIII).

The reaction is usually carried out in a conventional solvent such as acetone, dioxane, toluene, methylene chloride, ethylene chloride, tetrahydrofuran, or any other solvent which does not adversely influence the reaction.

The reaction temperature is not critical and the reaction is usually carried out under cooling to heating.

Process B

The compound (II) or a salt thereof can be prepared by subjecting the compound (IIb) or a salt thereof to elimination reaction of the carboxy protective group.

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid including Lewis acid. Suitable base may include an inorganic base and an organic base such as an alkali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), or the like.

Suitable acid may include an organic acid (e.g. formic acid, acetic acid, propionic acid, trichloroacetic acid, trifluoroacetic acid, etc.) and an inorganic acid (e.g. hydrochloric acid, hydrobromic acid, sulfuric acid, etc.).

Reduction can be applied preferably for elimination of the protective group such as 4-nitrobenzyl, 2-iodoethyl, 2,2,2-trichloroethyl, or the like. The reduction method applicable for the elimination reaction may include, for example reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium-carbon, etc.).

The reaction is usually carried out in a solvent such as water, an alcohol (e.g. methanol, ethanol, etc.), methylene chloride, tetrahydrofuran, a mixture thereof or any other solvent which does not adversely influence the reaction. A liquid base or acid can be also used as the solvent. The reaction temperature is not critical and the reaction is usually carried out under cooling to heating.

The object compound (I) and -pharmaceutically acceptable salt thereof are antagonists of PAF and therefore useful as a medicine for preventing and treating diseases such as allergic manifestation (e.g. asthma, etc.), thrombosis, shock (e.g. anaphylatic shock, anesthetic shock, cardiogenic shock, endotoxin shock, etc.), DIC (disseminated intravascular coagulation), nephropathy, nephritis, autoimmune diseases (e.g. rheumatism, etc.), ulcer (e.g. gastric ulcer, etc.), ischemia, cardiac infarction, septicemia or the like, and useful as an immunosuppressant in transplantation.

The following Tests are given for the purpose of illustrating antagonism of the compound (I) against PAF.

Test 1 (Inhibition of platelet aggregation)

Test method

Blood was collected through the polyethylene catheter introduced into the carotid artery of male Japanese white rabbit (2.5 to 3 kg body weight). The blood was anticoagulated with 1 volume of 3.8% sodium citrate to 9 volume of blood. Platelet rich plasma (PRP) was prepared by centrifugation of the blood at 150 g for 10 minutes at room temperature. The PRP was diluted with platelet poor plasma obtained by further centrifugation of the blood at 1,000 g for 20 minutes. The platelet number was $5 \times 10^5$ cells/mm$^3$. Platelet aggregation induced with PAF [1-O-hexadecyl-2-O-acetyl-sn-glycero-3-phosphorylcholine] was measured by the nephelometric technique of Born and Cross [cf. Journal of Physiology 168, 178–188 (1963)] using HKK Hema tracer (trade name, made by Niko Bioscience Inc.).

Activity of inhibitor was expressed as $IC_{50}$ value, i.e. concentration required to inhibit the platelet aggregation response by 50%. The final concentration of PAF was usually 32 nM.

Test compound

2'-(2-Chlorophenylmethyl)-4,5-dihydro-4-oxo-5-{2-(N,N-dimethylamino)ethyl}spiro[1,5-benzothiazepine-2(3H), 1'-cyclohexane] 1-oxide Test result $IC_{50}$: 0.17 μg/ml.

Test 2

Inhibition of PAF-induced vascular permeability increase:

Test method

PAF (50 ng) was injected intradermally to the depilated back of 6-week-old male ddY mice. Evan's blue (1 mg) was injected intravenously 5 minutes before the PAF injection, and the test compound was administered intraperitoneally 5 minutes before the Evan's blue injection. Thirty minutes later, the animals were killed and the area of dye leakage was measured.

The inhibition was expressed as $ED_{50}$ value, i.e. effective dose (mg/kg) required to inhibit PAF-induced vascular permeability increase by 50%.

Test Compound 1-(3-Chlorophenylmethyl)-10-(3-pyridylmethyl)-11-oxo-7-thia-10-azaspiro[5.6]dodecane 7,7-dioxide

Test result $ED_{50}$: 2.9 mg/kg.

Test 3

Effect of the test compound on PAF-induced bronchoconstriction in the guinea-pig

Test method

Male Hartley guinea-pigs (400–500 g) were anesthetized with sodium pentobarbital (25 mg/kg, intraperitoneally). The right jugular vein was catheterized for injection of PAF (0.64 μg/ml, 1 ml/kg), and the animals were tracheotomized and ventilated with a respiratory pump (Harvard B-34, 5 ml/stroke, 60 strocks/minutes).

The test compound was administered orally 30 minutes before challenge with PAF.

Test compound (1S,6S)-1-phenylmethyl-10-(3-pyridylmethyl)-11-oxo-7-thia-10-azaspiro[5.6]dodecane 7,7-dioxide

Test result $ED_{50}$: 3.7 mg/kg.

($ED_{50}$: effective dose of the test compound to inhibit the PAF-induced bronchoconstriction by 50%).

Test 4

Effect of the test compound on the endotoxin-induced disseminated intravascular coagulation:

Test method

Conscious male Wister rats, 150–200 g body weight, 7 weeks old, were used in the experiment on endotoxin-induced disseminated intravascular coagulation (DIC). The animals were fasted before the experiment. A 10 mg/kg dose of endotoxin (*E. coli*) dissolved in saline was given as an injection via tail vein. Test compound was given orally 60 minutes before and 6 hours after endotoxin. The intravenous administration of the test compound into a tail vein was simultaneous with intravenous injection of endotoxin.

Arterial blood samples were taken 4 hours (Test compound; intravenously) and 24 hours (Test compound; orally) after endotoxin for measurements of serum FDP (fibrin degradation products), respectively. FDP was determined by the latex aggregation test.

Test compound (1S,6S)-1-Phenylmethyl-10-(3-pyridylmethyl)-11-oxo-7-thia-10-azaspiro[5.6]dodecane 7,7-dioxide

| Dose route | Test result $ED_{50}$ (mg/kg) |
| --- | --- |
| oral | 6.8 |
| intravenous | 2.4 |

Test 5

Effect of the test compound on the PAF-induced lethality in rats:

Test method

Conscious male Wistar rats, 150–200 g body weight, 7 weeks old, were used in the experiment on PAF-induced lethality. The animals were fasted before the experiment. Test compound was given orally 60 minutes before (or intravenously simultaneously with) intravenous PAF injection (10 μg/kg) into a tail vein. Survival of the animals was recorded for 24 hours after intravenous PAF injection.

Test compound (1S,6S)-1-Phenylmethyl-10-(3-pyridylmethyl)-11-oxo-7-thia-10-azaspiro[5.6]dodecane 7,7-dioxide

| Dose route | Test result $ED_{50}$ (mg/kg) |
| --- | --- |
| oral | 2.0 |
| intravenous | 1.0 |

The compound (I) or pharmaceutically acceptable salt thereof in admixture with -pharmaceutically acceptable carriers can be administered orally or parenterally to mammals including human being in a form of a pharmaceutical composition such as injections, capsules, tablets, granules, powders, buccal tablets, sublingual tablets, inhalant, solution or the like.

The pharmaceutically acceptable carriers may include various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropyl-starch, sodium glycole-starch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, ammonium salt of glycyrrhizin, glycine, organge powders, etc.), preservative (sodium benzoate, sodium bisulfate, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent [e.g. surface active agent, etc.], aqueous diluting agent (e.g. water), base wax (e.g. cacao butter, polyethyleneglycol, white petrolatum, etc.).

A dosage of the object compound is to be varied depending on various factors such as kind of diseases, weight and/or age of a patient, and further the kind of administration route.

The optimal dosage of the compound (I) is usually selected from a dose range of 1 mg–1 g/day, preferably 10 mg–500 mg/day.

The total daily amount mentioned above may be divisionally given to the patient at the interval of 6–12 hours per day.

The following Examples and Preparation are given for the purpose of illustrating this invention.

EXAMPLE 1

(1) A mixture of 2-phenylmethyl-1-carboxymethylenecyclohexane (10 g) and 2-aminoethanethiol (10 g) in N,N-dimethylformamide (10 ml) was refluxed for 20 hours under nitrogen atmosphere. The mixture was cooled to 0° C. and diluted with ethyl acetate (100 ml), and the mixture was washed with 1N hydrochloric acid (100 ml), water (100 ml), a saturated aqueous solution of sodium bicarbonte (100 ml) and brine (100 ml). The organic layer was dried over magnesium sulfate and concentrated in vacuo. The residue was triturated with diethyl ether to give 1-phenylmethyl-11-oxo-7-thia-10-azaspiro[5.6]dodecane (6.6 g).

mp: 130°–135° C.

The following compounds were obtained according to a similar manner to that of Example 1(1).

(2) 1-(4-Chlorophenylmethyl)-11-oxo-7-thia-10-azaspiro[5.6]dodecane
mp: 169°–170° C.

(3) 1-(4-Methoxyphenylmethyl)-11-oxo-7-thia-10-azaspiro[5.6]dodecane
mp: 153°–155° C.

(4) 1-(4-Methylphenylmethyl)-11-oxo-7-thia-10-azaspiro[5.6]dodecane
mp: 196°–198° C.

(5) 1-(2-Methylphenylmethyl)-11-oxo-7-thia-10-azaspiro[5.6]dodecane
mp: 158°–159° C.

(6) 1-(3-Chlorophenylmethyl)-11-oxo-7-thia-10-azaspiro[5.6]dodecane
mp: 130°–135° C.

$^1$H—NMR (CDCl$_3$, δ): 1.0–1.45 (2H, m), 1.5–2.1 (7H, m), 2.4 (1H, m), 2.6 (1H, m), 2.8–3.2 (3H, m), 3.4–3.8 (3H, m), 6.5 (1H, br s), 7.0–7.3 (4H, m)

(7) 1-(2-Chlorophenylmethyl)-11-oxo-7-thia-10-azaspiro[5.6]dodecane
mp: 154°–155° C.

(8) 1-(3-Fluorophenylmethyl)-11-oxo-7-thia-10-azaspiro[5.6]dodecane
mp: 133°–137° C.

(9) 1-(2-Fluorophenylmethyl)-11-oxo-7-thia-10-azaspiro[5.6]dodecane
mp: 125°–128° C.

(10) 1-(2,6-Dichlorophenylmethyl)-11-oxo-7-thia-10-azaspiro[5.6]dodecane
mp: 210°–215° C.

(11) 1-(1-Naphthylmethyl)-11-oxo-7-thia-10-azaspiro[5.6]dodecane
mp: 174°–176° C.

(12) 1-(2-Bromophenylmethyl)-11-oxo-7-thia-10-azaspiro[5.6]dodecane
mp: 145°–148° C.

EXAMPLE 2

(1) A mixture of 2-phenylmethyl-1-carboxymethylenecyclohexane (3.0 g) and 2-aminothiophenol (5.0 g) in N,N-dimethylformamide (3 ml) was refluxed for 20 hours under nitrogen atmosphere. The mixture was cooled to 0° C. and diluted with ethyl acetate (30 ml) and the mixture was washed with 1N hydrochloric acid (30 ml), water (30 ml), a saturated aqueous solution of sodium bicarbonate (30 ml) and brine (30 ml). The organic layer was dried over magnesium sulfate and concentrated in vacuo. The residue was triturated with diethyl ether to give 2'-phenylmethyl-4,5-dihydro-4-oxospiro[1,5-benzothiazepine-2(3H), 1'-cyclohexane] (2.2 g).

mp: 173°–177° C.

$^1$H—NMR (CDCl$_3$, δ): 1.0–2.1 (9H, m), 2.4 (1H, br), 2.7 (2H, ABq), 3.3 (1H, d), 7.0–7.4 (7H, m), 7.7 (1H, dd), 8.0 (1H, br s).

The following compounds were obtained according to a similar manner to that of Example 2(1).

(2) 2'-(4-Methoxyphenylmethyl)-4,5-dihydro-4-oxospiro-[1,5-benzothiazepine-2(3H), 1'-cyclohexane]
mp: 173°–175° C.

(3) 2'-(4-Chlorophenylmethyl)-4,5-dihydro-4-oxospiro-[1,5-benzothiazepine-2(3H), 1'-cyclohexane]
mp: 193°–195° C.

(4) 2'-(4-Methylphenylmethyl)-4,5-dihydro-4-oxospiro-[1,5-benzothiazepine-2(3H), 1'-cyclohexane]
mp: 188°–190° C.

(5) 2'-(2-Chlorophenylmethyl)-4,5-dihydro-4-oxospiro-[1,5-benzothiazepine-2(3H), 1'-cyclohexane]
mp: 178°–182° C.

EXAMPLE 3

(1) To a solution of 1-phenylmethyl-11-oxo-7-thia-10-azaspiro[5.6]dodecane (2.5 g) in methylene chloride (80 ml) was added 80% m-chloroperbenzoic acid (3.8 g) at 0° C. After one hour, a saturated aqueous solution (50 ml) of sodium sulfite was added to the solution. The organic layer was washed with brine (50 ml), dried over magnesium sulfate and concentrated in vacuo. The residue was triturated with diethyl ether to give 1-phenylmethyl-11-oxo-7-thia-10-azaspiro[5.6]dodecane 7,7-dioxide (2.37 g).

mp: 130°–135° C.

The following compounds were obtained according to a similar manner to that of Example 3(1).

(2) 1-(3-Chlorophenylmethyl)-11-oxo-7-thia-10-azaspiro[5.6]dodecane 7,7-dioxide
mp: 175°–178° C.

$^1$H—NMR (CDCl$_3$, δ): 1.0–1.5 (2H, m), 1.5–2.1 (4H, m), 2.2 (1H, m), 2.5 (1H, br t), 2.7–3.2 (3H, m), 3.3–3.6 (4H, m), 3.8–4.1 (2H, m), 6.4 (1H, br s), 7.1–7.4 (4H, m)

(3) 1-(2-Methylphenylmethyl)-11-oxo-7-thia-10-azaspiro[5.6]dodecane 7,7-dioxide
mp: 206°–207° C.

(4) 1-(2-Chlorophenylmethyl)-11-oxo-7-thia-10-azaspiro[5.6]dodecane 7,7-dioxide
mp: 184°–187° C.

(5) 1-(4-Methylphenylmethyl)-11-oxo-7-thia-10-azaspiro[5.6]dodecane 7,7-dioxide
mp: 232°–234° C.

(6) 1-(4-Methoxyphenylmethyl)-11-oxo-7-thia-10-azaspiro[5.6]dodecane 7,7-dioxide
mp: 209°–214° C.

(7) 1-(4-Chlorophenylmethyl)-11-oxo-7-thia-10-azaspiro[5.6]dodecane 7,7-dioxide
mp: 195°–197° C.

(8) 1-Phenylmethyl-10-(4-pyridylmethyl)-11-oxo-7-thia-10-azaspiro[5.6]dodecane 7,7-dioxide
IR (neat): 1640 cm$^{-1}$.

(9) 2'-Phenylmethyl-4,5-dihydro-4-oxospiro-[1,5-benzothiazepine-2(3H), 1'-cyclohexane] 1,1-dioxide
mp: >250° C.

(10) 2'-Phenylmethyl-4,5-dihydro-4-oxo-5-(4-pyridylmethyl)spiro[1,5-benzothiazepine-2(3H), 1'-cyclohexane] 1,1-dioxide IR (neat): 1660 cm$^{-1}$.

(11) 1-(3-Fluorophenylmethyl)-11-oxo-7-thia-10-azaspiro[5.6]dodecane 7,7-dioxide mp: 118°–121° C.

(12) 1-(2-Fluorophenylmethyl)-11-oxo-7-thia-10-azaspiro[5.6]dodecane 7,7-dioxide mp: 103°–106° C.

(13) 1-(2-Bromophenylmethyl)-11-oxo-7-thia-10-azaspiro[5.6]dodecane 7,7-dioxide mp: 215°–220° C.

(14) 1-(1-Naphthylmethyl)-11-oxo-7-thia-10-azaspiro[5.6]dodecane 7,7-dioxide mp: 175°–180° C.

(15) 1-(2,6-Dichlorophenylmethyl)-11-oxo-7-thia-10-azaspiro[5.6]dodecane 7,7-dioxide mp: 225°–228° C.

EXAMPLE 4

(1) To a solution of 2'-phenylmethyl-4,5-dihydro-4-oxospiro[1,5-benzothiazepine-2(3H), 1'-cyclohexane] (5.0 g) in methylene chloride (150 ml) was added 80% m-chloroperbenzoic acid (3.9 g) at 0° C. After fifteen minutes, a saturated aqueous solution (150 ml) of sodium sulfite was added to the solution. The organic layer was washed with brine, dried over magnesium sulfate and concentrated in vacuo. The residue was triturated with diisopropyl ether to give 2'-phenylmethyl-4,5-dihydro-4-oxospiro[1,5-benzothiazepine-2(3H), 1'-cyclohexane] 1-oxide mp: 180° C. (dec.).

The following compounds were obtained according to a similar manner to that of Example 4(1).

(2) 1-Phenylmethyl-11-oxo-7-thia-10-azaspiro[5.6]dodecane 7-oxide mp: 172°–175° C.

(3) 2'-(2-Chlorophenylmethyl)-4,5-dihydro-4-oxospiro-[1,5-benzothiazepine-2(3H), 1'-cyclohexane] 1-oxide mp: 184° C. (dec.).

(4) 2'-(4-Methoxyphenylmethyl)-4,5-dihydro-4-oxospiro-[1,5-benzothiazepine-2(3H), 1'-cyclohexane] 1-oxide mp: 175° C. (dec.).

(5) 2'-(4-Methylphenylmethyl)-4,5-dihydro-4-oxospiro-[1,5-benzothiazepine-2(3H), 1'-cyclohexane] 1-oxide mp: 190° C. (dec.).

(6) 2'-(4-Chlorophenylmethyl)-4,5-dihydro-4-oxospiro-[1,5-benzothiazepine-2(3H), 1'-cyclohexane] 1-oxide mp: 175° C. (dec.).

(7) 2'-Phenylmethyl-4,5-dihydro-4-oxo-5-{2-N,N-dimethylamino)ethyl}spiro[1,5-benzothiazepine-2(3H), 1'-cyclohexane] 1-oxide hydrochloride IR (neat): 1660 cm$^{-1}$.

$^1$H—NMR (CDCl$_3$, δ): 1.0–3.6 (21H, m), 4.3 (1H, m), 4.6 (1H, m), 7.1–7.9 (9H, m).

EXAMPLE 5

(1) A stirred suspension of sodium hydride (20 mg) in dimethylsulfoxide (2 ml) was heated at 60° C. under nitrogen atmosphere. After one hour, 1-phenylmethyl-11-oxo-7-thia-10-azaspiro[5.6]dodecane 7,7-dioxide (0.20 g) and 2-pyridylmethyl chloride (0.2 ml) were added to the solution and the mixture was allowed to stand at room temperature for one hour. The mixture was diluted with ethyl acetate (20 ml) and washed with a saturated aqueous solution (20 ml) of sodium bicarbonate, water (20 ml) and brine (20 ml). The organic layer was dried over magnesium sulfate and concentrated in vacuo. The residue was purified with silica gel (6 g) column chromatography (ethyl acetate) to give 1-phenylmethyl-10-(2-pyridylmethyl)-11-oxo-7-thia-10-azaspiro[5.6]dodecane 7,7-dioxide (0.21 g).

IR (neat): 1640 cm$^{-1}$.

The following compounds were obtained according to a similar manner to that of Example 5(1).

(2) 1-Phenylmethyl-10-{3-(N,N-dimethylamino)propyl}-11-oxo-7-thia-10-azaspiro[5.6]dodecane 7,7-dioxide IR (neat): 1640 cm$^{-1}$.

(3) 1-Phenylmethyl-10-{2-(N,N-dimethylamino)ethyl}-11-oxo-7-thia-10-azaspiro[5.6]dodecane 7,7-dioxide IR (neat): 1640 cm$^{-1}$.

(4) 1-(2-Chlorophenylmethyl)-10-(3-pyridylmethyl)-11-oxo-7-thia-10-azaspiro[5.6]dodecane 7,7-dioxide mp: 130°–131° C.

IR (Nujol): 1640 cm$^{-1}$.

(5) 1-(2-Chlorophenylmethyl)-10-(4-pyridylmethyl)-11-oxo-7-thia-10-azaspiro[5.6]dodecane 7,7-dioxide mp: 155°–158° C.

IR (Nujol): 1640 cm$^{-1}$.

(6) 1-(3-Chlorophenylmethyl)-10-(3-pyridylmethyl)-11-oxo-7-thia-10-azaspiro[5.6]dodecane 7,7-dioxide mp: 165°–170° C.

IR (Nujol): 1640 cm$^{-1}$.

$^1$H—NMR (CDCl$_3$, δ): 1.0–1.4 (2H, m), 1.6–2.1 (6H, m), 2.5 (1H, br t), 2.8 (1H, dd), 3.1 (2H, m), 3.55 (2H, m), 4.0 (1H, d), 4.2 (1H, dd), 4.7 (2H, s), 7.1–7.4 (5H, m), 7.7 (1H, m), 8.6 (2H, m).

(7) 1-(2-Methylphenylmethyl)-10-(3-pyridylmethyl)-11-oxo-7-thia-10-azaspiro[5.6]dodecane 7,7-dioxide IR (neat): 1640 cm$^{-1}$.

(8) 1-(4-Methoxyphenylmethyl)-10-(4-pyridylmethyl)-11-oxo-7-thia-10-azaspiro[5.6]dodecane 7,7-dioxide IR (neat): 1640 cm$^{-1}$.

(9) 1-(4-Methylphenylmethyl)-10-(4-pyridylmethyl)-11-oxo-7-thia-10-azaspiro[5.6]dodecane 7,7-dioxide mp: 198°–204° C.

IR (Nujol): 1640 cm$^{-1}$.

(10) 1-(4-Chlorophenylmethyl)-10-(4-pyridylmethyl)-11-oxo-7-thia-10-azaspiro[5.6]dodecane 7,7-dioxide mp: 183°–186° C.

IR (Nujol): 1640 cm$^{-1}$.

(11) 1-(4-Methylphenylmethyl)-10-(3-pyridylmethyl)-11-oxo-7-thia-10-azaspiro[5.6]dodecane 7,7-dioxide mp: 162°–165° C.

IR (Nujol): 1640 cm$^{-1}$.

(12) 1-Phenylmethyl-10-(3-pyridylmethyl)-11-oxo-7-thia-10-azaspiro[5.6]dodecane 7,7-dioxide mp: 168°–174° C.

IR (Nujol): 1640 cm$^{-1}$.

$^1$H—NMR (CDCl$_3$, δ): 1.0–1.4 (2H, m), 1.6–2.1 (6H, m), 2.5 (1H, br t), 2.8 (1H, dd), 3.1 (2H, m), 3.55 (2H, m), 4.0 (1H, d), 4.2 (1H, dd), 4.7 (2H, s), 7.1–7.35 (6H, m), 7.7 (1H, m), 8.6 (2H, m).

(13) 1-(4-Chlorophenylmethyl)-10-(3-pyridylmethyl)-11-oxo-7-thia-10-azaspiro[5.6]dodecane 7,7-dioxide mp: 155°–157° C.

IR (Nujol): 1640 cm$^{-1}$.

(14) 1-(4-Methoxyphenylmethyl)-10-(3-pyridylmethyl)-11-oxo-7-thia-10-azaspiro[5.6]dodecane 7,7-dioxide
mp: 142°–144° C.
IR (Nujol): 1640 cm$^{-1}$.

(15) 1-Phenylmethyl-10-{4-(3-pyridyl)butyl}-11-oxo-7-thia-10-azaspiro[5.6]dodecane 7,7-dioxide
IR (neat): 1640 cm$^{-1}$.

(16) 1-Phenylmethyl-10-(4-pyridylmethyl)-11-oxo-7-thia-10-azaspiro[5.6]dodecane
IR (neat): 1640 cm$^{-1}$.

(17) 1-Phenylmethyl-10-(3-pyridylmethyl)-11-oxo-7-thia-10-azaspiro-[5.6]dodecane
IR (neat): 1640 cm$^{-1}$.

(18) 1-Phenylmethyl-10-{3-(N,N-dimethylamino)propyl}-11-oxo-7-thia-10-azaspiro[5.6]dodecane
IR (neat): 1640 cm$^{-1}$.

(19) 1-Phenylmethyl-10-(2-pyridylmethyl)-11-oxo-7-thia-10-azaspiro[5.6]dodecane
IR (neat): 1640 cm$^{-1}$.

(20) 1-Phenylmethyl-10-{3-(N,N-dimethylamino)propyl}-11-oxo-7-thia-10-azaspiro[5.6]dodecane 7-oxide
IR (neat): 1640 cm$^{-1}$.

(21) 1-Phenylmethyl-10-(4-pyridylmethyl)-11-oxo-7-thia-10-azaspiro[5.6]dodecane 7-oxide
IR (neat): 1640 cm$^{-1}$.

(22) 1-Phenylmethyl-10-{2-(N,N-dimethylamino)ethyl}-11-oxo-7-thia-10-azaspiro[5.6]dodecane 7-oxide
IR (neat): 1640 cm$^{-1}$.

(23) 1-Phenylmethyl-10-(3-pyridylmethyl)-11-oxo-7-thia-10-azaspiro[5.6]dodecane 7-oxide
IR (neat): 1640 cm$^{-1}$.

(24) 1-Phenylmethyl-10-(2-pyridylmethyl)-11-oxo-7-thia-10-azaspiro[5.6]dodecane 7-oxide
IR (neat): 1640 cm$^{-1}$.

(25) 1-Phenylmethyl-10-{2-(N,N-dimethylamino)ethyl}-11-oxo-7-thia-10-azaspiro[5.6]dodecane
IR (neat): 1640 cm$^{-1}$.

(26) 2'-Phenylmethyl-4,5-dihydro-4-oxo-5-(4-pyridylmethyl)spiro[1,5-benzothiazepine-2(3H), 1'-cyclohexane] 1,1-dioxide
mp: >250° C.
IR (Nujol): 1660 cm$^{-1}$.

(27) 2'-Phenylmethyl-4,5-dihydro-4-oxo-5-{2-(N,N-dimethylamino)ethyl}spiro[1,5-benzothiazepine-2(3H), 1'-cyclohexane] hydrochloride
mp: 120°–125° C.
IR (Nujol): 1660 cm$^{-1}$.
$^1$H—NMR (CDCl$_3$, δ): 1.0–3.6 (21H, m), 4.3 (1H, m), 4.6 (1H, m), 7.1–7.9 (9H, m).

(28) 2'-Phenylmethyl-4,5-dihydro-4-oxo-5-{2-(N,N-dimethylamino)ethyl}spiro[1,5-benzothiazopine-2(3H), 1'-cyclohexane] 1,1-dioxide
mp: 188°–190° C.
IR (Nujol): 1660 cm$^{-1}$.

(29) 2'-Phenylmethyl-4,5-dihydro-4-oxo-5-{3-(N,N-dimethylamino)propyl}spiro[1,5-benzothiazepine-2(3H), 1'-cyclohexane]
IR (neat): 1660 cm$^{-1}$.

(30) 2'-Phenylmethyl-4,5-dihydro-4-oxo-5-{3-(N,N-dimethylamino)propyl}spiro[1,5-benzothiazepine-2(3H), 1'-cyclohexane] 1-oxide
IR (neat): 1640 cm$^{-1}$.

(31) 2'-Phenylmethyl-4,5-dihydro-4-oxo-5-{3-(N,N-dimethylamino)propyl}spiro[1,5-benzothiazepine-2(3H), 1'-cyclohexane] 1,1-dioxide
mp: 191°–194° C.
IR (Nujol): 1660 cm$^{-1}$.

(32) 2'-Phenylmethyl-4,5-dihydro-4-oxo-5-(2-pyridylmethyl)spiro[1,5-benzothiazepine-2(3H), 1'-cyclohexane]
IR (neat): 1660 cm$^{-1}$.

(33) 2'-Phenylmethyl-4,5-dihydro-4-oxo-5-(2-pyridylmethyl)spiro[1,5-benzothiazepine-2(3H), 1'-cyclohexane] 1-oxide
IR (neat): 1660 cm$^{-1}$.

(34) 2'-Phenylmethyl-4,5-dihydro-4-oxo-5-(2-pyridylmethyl)spiro[1,5-benzothiazepine-2(3H), 1'-cyclohexane] 1,1-dioxide
IR (neat): 1660 cm$^{-1}$.

(35) 2'-Phenylmethyl-4,5-dihydro-4-oxo-5-(3-pyridylmethyl)spiro[1,5-benzothiazepine-2(3H), 1'-cyclohexane]
IR (neat): 1660 cm$^{-1}$.

(36) 2'-Phenylmethyl-4,5-dihydro-4-oxo-5-(3-pyridylmethyl)spiro[1,5-benzothiazepine-2(3H), 1'-cyclohexane] 1-oxide
IR (neat): 1660 cm$^{-1}$.

(37) 2'-Phenylmethyl-4,5-dihydro-4-oxo-5-(3-pyridylmethyl)spiro[1,5-benzothiazepine-2(3H), 1'-cyclohexane] 1,1-dioxide
mp: 200°–225° C.
IR (Nujol): 1660 cm$^{-1}$.

(38) 2'-Phenylmethyl-4,5-dihydro-4-oxo-5-(4-pyridylmethyl)spiro[1,5-benzothiazepine-2(3H), 1'-cyclohexane]
IR (neat): 1660 cm$^{-1}$.

(39) 2'-Phenylmethyl-4,5-dihydro-4-oxo-5-(4-pyridylmethyl)spiro[1,5-benzothiazepine-2(3H), 1'-cyclohexane] 1-oxide
IR (neat): 1660 cm$^{-1}$.

(40) 2'-(4-Chlorophenylmethyl)-4,5-dihydro-4-oxo-5-{2-(N,N-dimethylamino)ethyl}spiro[1,5-benzothiazepine-2(3H), 1'-cyclohexane] 1-oxide
IR (neat): 1660 cm$^{-1}$.

(41) 2'-(4-Methylphenylmethyl)-4,5-dihydro-4-oxo-5-{2-(N,N-dimethylamino)ethyl}spiro[1,5-benzothiazepine-2(3H), 1'-cyclohexane] 1-oxide
IR (neat): 1660 cm$^{-1}$.

(42) 2'-(4-Methoxyphenylmethyl)-4,5-dihydro-4-oxo-5-{2-(N,N-dimethylamino)ethyl}spiro[1,5-benzothiazepine-2(3H), 1'-cyclohexane] 1-oxide
IR (neat): 1660 cm$^{-1}$.

(43) 2'-(2-Chlorophenylmethyl)-4,5-dihydro-4-oxo-5-{2-(N,N-dimethylamino)ethyl}spiro[1,5-benzothiazepine-2(3H), 1'-cyclohexane] 1-oxide
IR (neat): 1660 cm$^{-1}$.

(44) 1-Phenylmethyl-10-[(2-methyl-3-pyridyl)methyl]-11-oxo-7-thia-10-azaspiro[5.6]dodecane 7,7-dioxide
mp: 211°–214° C.
IR (Nujol): 1655 cm$^{-1}$.

(45) 1-Phenylmethyl-10-[(2-methyl-5-pyridyl)methyl]-11-oxo-7-thia-10-azaspiro[5.6]dodecane 7,7-dioxide
mp: 192°–195° C.
IR (Nujol): 1635 cm$^{-1}$.

(46) 1-Phenylmethyl-10-[(2-chloro-3-pyridyl)methyl]-11-oxo-7-thia-10-azaspiro[5.6]dodecane 7,7-dioxide
mp: 213°–215° C.
IR (Nujol): 1650 cm$^{-1}$.

(47) 1-Phenylmethyl-10-[(2-chloro-5-pyridyl)methyl]-11-oxo-7-thia-10-azaspiro[5.6]dodecane 7,7-dioxide mp: 183°–186° C.
IR (Nujol): 1635 cm$^{-1}$.

(48) 1-Phenylmethyl-10-[(2-methoxy-5-pyridyl)methyl]-11-oxo-7-thia-10-azaspiro[5.6]dodecane 7,7-dioxide
mp: 156°–158° C.
IR (Nujol): 1640 cm$^{-1}$.

(49) 1-(3-Fluorophenylmethyl)-10-(3-pyridylmethyl)-11-oxo-7-thia-10-azaspiro[5.6]dodecane 7,7-dioxide
mp: 173°–175° C.
IR (Nujol): 1635 cm$^{-1}$.

(50) 1-(2-Fluorophenylmethyl)-10-(3-pyridylmethyl)-11-oxo-7-thia-10-azaspiro[5.6]dodecane 7,7-dioxide
mp: 159°–160° C.
IR (Nujol): 1635 cm$^{-1}$.

(51) 1-Phenylmethyl-10-(3-quinolylmethyl)-11-oxo-7-thia-10-azaspiro[5.6]dodecane 7,7-dioxide
mp: 205°–208° C.
IR (Nujol): 1640 cm$^{-1}$.

(52) 1-Phenylmethyl-10-(2-quinoxalinylmethyl)-11-oxo-7-thia-10-azaspiro[5.6]dodecane 7,7-dioxide
IR (Neat): 1640 cm$^{-1}$.

(53) 1-Phenylmethyl-10-(5-thiazolylmethyl)-11-oxo-7-thia-10-azaspiro[5.6]dodecane 7,7-dioxide
mp: 195°–198° C.
IR (Nujol): 1640 cm$^{-1}$.

(54) 1-Phenylmethyl-10-(2-morpholinoethyl)-11-oxo-7-thia-10-azaspiro[5.6]dodecane 7,7-dioxide
mp: 150°–152° C.
IR (Nujol): 1640 cm$^{-1}$.

(55) 1-(2-Bromophenylmethyl)-10-(3-pyridylmethyl)-11-oxo-7-thia-10-azaspiro[5.6]dodecane 7,7-dioxide
IR (Nujol): 1640 cm$^{-1}$.

(56) 1-(2,6-Dichlorophenylmethyl)-10-(3-pyridylmethyl)-11-oxo-7-thia-10-azaspiro[5.6]dodecane 7,7-dioxide
IR (Nujol): 1640 cm$^{-1}$.

(57) 1-(1-Naphthylmethyl)-10-(3-pyridylmethyl)-11-oxo-7-thia-10-azaspiro[5.6]dodecane 7,7-dioxide
IR (Nujol): 1640 cm$^{-1}$.

EXAMPLE 6

A suspension of sodium hydride (30 mg) in dimethylsulfoxide (5 ml) was heated at 60° C. under nitrogen atmosphere. After one hour, 1-phenylmethyl-11-oxo-7-thia-10-azaspiro[5.6]dodecane 7,7-dioxide (0.32 g) and 1,4-dibromobutane (5 ml) were added to the mixture at room temperature. After two hours, the mixture was diluted with ethyl acetate (30 ml) and washed with water (30 ml) and brine (30 ml). The organic layer was dried over magnesium sulfate and concentrated in vacuo. The residue was purified with silica gel column (10 g) (ethyl acetate:hexane=1:1) to give 1-phenylmethyl-10-(4-bromobutyl)-11-oxo-7-thia-10-azaspiro[5.6]dodecane 7,7-dioxide (0.35 g).
IR (neat): 1640 cm$^{-1}$.

EXAMPLE 7

1-Phenylmethyl-10-(4-bromobutyl)-11-oxo-7-thia-10-azaspiro[5.6]dodecane 7,7-dioxide (0.34 g) in pyridine (5 ml) was refluxed for thirty minutes. Then pyridine was evaporated in vacuo to give 1-phenylmethyl-10-{4-(1-pyridinio)butyl}-11-oxo-7-thia-10-azaspiro[5.6]dodecane 7,7-dioxide bromide (0.42 g).
IR (neat): 1635 cm$^{-1}$.

Each of all the compounds obtained in the forementioned Examples is a mixture of R and S isomers.

PREPARATION 1

To a suspension of sodium hydride 14.4 g, 60% dispersion in mineral oil) in toluene (400 ml) was added dropwise triethyl phosphonoacetate (90 ml) in toluene (100 ml) at 30°–35° C. under nitrogen atmosphere. The mixture was stirred for 1 hour at room temperature. To this nearly clear solution was added dropwise (2S)-2-phenylmethylcyclohexanone (56.5 g) in toluene (100 ml) at room temperature and the mixture was stirred at 60° C. for 2 hours. After cooling at 0° C., the mixture was washed with 1N hydrochloric acid (500 ml), water (500 ml), saturated aqueous sodium bicarbonate (500 ml) and brine (500 ml). The organic layer was dried over anhydrous magnesium sulfate and concentrated in vacuo. The residue was dissolved in methanol (300 ml) and 5N aqueous potassium hydroxide (300 ml) and refluxed for 2 hours. The mixture was concentrated to half volume in vacuo and acidified (pH=3) with concentrated hydrochloric acid. The mixture was extracted with ethyl acetate-diisopropyl ether (1:1, 500 ml) and the organic layer was extracted with 1N aqueous sodium hydroxide (250 ml×2). The aqueous layer was acidified (pH=3) with concentrated hydrochloric acid and extracted with ethyl acetate-diisopropyl ether (1:1, 500 ml), and the extract was dried over anhydrous magnesium sulfate and concentrated in vacuo. The residue was triturated with hexane to give (2S)-2-phenylmethyl-1-carboxymethylenecyclohexane (38.6 g).
mp: 100°–105° C.
$[\alpha]_D = +31.4°$ (C=1.0, CH$_3$OH)
$^1$H—NMR (CDCl$_3$, δ): 1.3–3.2 (11H, m), 5.6 (1H, s), 7.0–7.4 (5H, m).

EXAMPLE 8

A mixture of (2S)-2-phenylmethyl-1-carboxymethylenecyclohexane (38.6 g) and 2-aminoethanethiol (40 g) in pyridine (40 ml) was refluxed for 15 hours under nitrogen atmosphere. This was cooled to 0° C., diluted with ethyl acetate (500 ml) and washed with 1N hydrochloric acid (500 ml×2), water (500 ml), saturated aqueous sodium bicarbonate (500 ml) and brine (500 ml). The organic layer was dried over anhydrous magnesium sulfate and concentrated in vacuo. The residue was dissolved in dry dichloromethane (400 ml). To the mixture was added m-chloroperbenzoic acid (80%, 108 g) at 0° C. After 1 hour, saturated aqueous sodium sulfite (400 ml) was added to the solution. The mixture was washed with 3N aqueous potassium hydroxide (400 ml×2) and brine (400 ml), dried over anhydrous magnesium sulfate and concentrated in vacuo. The residue was triturated with diethyl ether to give (1S,6S)-1-phenylmethyl-11-oxo-7-thia-10-azaspiro[5.6]dodecane 7,7-dioxide (40.0 g).
mp: 198°–201° C.
$^1$H—NMR (CDCl$_3$, δ): 0.9–1.5 (2H, m), 1.5–2.1 (4H, m), 2.2 (1H, m), 2.55 (2H, br t), 2.7–3.2 (3H, m), 3.3–3.6 (4H, m), 3.8–4.1 (2H, m), 7.0 (1H, br s), 7.1–7.4 (5H, m).

EXAMPLE 9

The following compounds were obtained according to a similar manner to that of Example 8.

(1) (1R,6R)-1-Phenylmethyl-11-oxo-7-thia-10-azaspiro[5.6]dodecane 7,7-dioxide
mp: 197°–200° C.
$^1$H—NMR (CDCl$_3$, δ): 0.9–1.5 (2H, m), 1.5–2.1 (4H, m), 2.2 (1H, m), 2.55 (1H, br t), 2.7–3.2 (3H, m), 3.3–3.6 (4H, m), 3.8–4.1 (2H, m), 7.0 (1H, br s), 7.1–7.4 (5H, m).

(2) (1S,6S)-1-(3-Chlorophenylmethyl)-11-oxo-7-thia-10-azaspiro[5.6]dodecane 7,7-dioxide
mp: 176°–180° C.

EXAMPLE 10

A stirred suspension of sodium hydride (5.5 g, 60% dispersion in mineral oil) in dimethyl sulfoxide (400 ml) was heated at 60° C. for 1 hour under nitrogen atmosphere. (1S,6S)-1-Phenylmethyl-11-oxo-7-thia-10-azaspiro[5.6]-dodecane 7,7-dioxide (40.0 g) and 3-pyridylmethyl chloride (25 g) were added to the nearly clear solution and the mixture was allowed to stand at room temperature for 15 minutes. The mixture was diluted with ethyl acetate (2 l) and washed with saturated aqueous sodium bicarbonate (2 l) and brine (2 l). The organic layer was dried over anhydrous magnesium sulfate and concentrated in vacuo. The residue was triturated with ethyl acetate and recrystallized from ethanol to give (1S,6S)-1-phenylmethyl-10-(3-pyridylmethyl)-11-oxo-7-thia-10-azaspiro[5.6]dodecane 7,7-dioxide (14.0 g).
mp: 220°–221° C.
IR (Nujol): 1640 cm$^{-1}$.
$[\alpha]_D = -28.9°$ (C=1.14, CH$_3$OH).
$^1$H—NMR (CDCl$_3$, $\delta$): 1.0–1.4 (2H, m), 1.6–2.1 (6H, m), 2.5 (1H, br t), 2.8 (1H, dd), 3.1 (2H, m), 3.55 (2H, m), 4.0 (1H, d), 4.2 (1H, dd), 4.7 (2H, s), 7.1–7.35 (6H, m), 7.7 (1H, m), 8.6 (2H, m).

EXAMPLE 11

The following compounds were obtained according to a similar manner to that of Example 10.

(1) (1S,6S)-1-Phenylmethyl-10-(4-pyridylmethyl)-11-oxo-7-thia-10-azaspiro[5.6]dodecane 7,7-dioxide
mp: 213°–215° C.
IR (Nujol): 1645 cm$^{-1}$.
$[\alpha]_D^{20} = -39.25°$ (C=1.0, CH$_3$OH).
$^1$H—NMR (CDCl$_3$, $\delta$): 1.00–1.40 (2H, m), 1.58–1.85 (4H, m), 1.90–2.10 (2H, m), 2.42–2.63 (1H, m), 2.73–2.92 (2H, m), 3.04–3.35 (2H, m), 3.40–3.60 (2H, m), 3.96 (1H, d, J=15 Hz), 4.18–4.36 (1H, m), 4.51 (1H, d, J=15 Hz), 4.88 (1H, d, J=15 Hz), 7.14–7.34 (7H, m), 8.57–8.68 (2H, m).

(2) (1S,6S)-1-(3-Chlorophenylmethyl)-10-(3-pyridylmethyl)-11-oxo-7-thia-10-azaspiro[5.6]dodecane 7,7-dioxide
mp: 220°–222° C.
IR (Nujol): 1635 cm$^{-1}$.
$[\alpha]_D^{23} = -20.67°$ (C=0.57, CH$_3$OH).

(3) (1S,6S)-1-Phenylmethyl-10-[(2-methyl-3-pyridyl)methyl]-11-oxo-7-thia-10-azaspiro[5.6]dodecane 7,7-dioxide
mp: 206°–208° C.
IR (Nujol): 1660 cm$^{-1}$.
$[\alpha]_D^{23} = -31.57°$ (C=1.0, CH$_3$OH).

(4) (1S,6S)-1-Phenylmethyl-10-(3-pyridylmethyl)-11-oxo-7-thia-10-azaspiro[5.6]dodecane 7,7-dioxide
mp: 220°–221° C.
IR (Nujol): 1640 cm$^{-1}$.
$[\alpha]_D = -28.9°$ (C=1.14, CH$_3$OH).

(5) (1R,6R)-1-Phenylmethyl-10-(3-pyridylmethyl)-11-oxo-7-thia-10-azaspiro[5.6]dodecane 7,7-dioxide
mp: 220°–221° C.
IR (Nujol): 1640 cm$^{-1}$.
$[\alpha]_D = +33.5°$ (C=1.0, CH$_3$OH).
$^1$H—NMR (CDCl$_3$, $\delta$): 1.0–1.4 (2H, m), 1.6–2.1 (6H, m), 2.5 (1H, br t), 2.8 (1H, dd), 3.1 (2H, m), 3.55 (2H, m), 4.0 (1H, d), 4.2 (1H, dd), 4.7 (2H, s), 7.1–7.35 (6H, m), 7.7 (1H, m), 8.6 (2H, m).

EXAMPLE 12

A solution of 4N hydrogen chloride in ethyl acetate (50 ml) was added to a solution of (1S,6S)-1-phenylmethyl-10-(3-pyridylmethyl)-11-oxo-7-thia-10-azaspiro[5.6]-dodecane 7,7-dioxide (12.6 g) in methylene chloride (130 ml) and the mixture was concentrated under reduced pressure. The residue was dissolved in ethyl alcohol (50 ml) and the solution was warmed at 80° C. Isopropyl alcohol (350 ml) was added dropwise to a solution and the mixture was refluxed for one hour. The mixture was cooled to 0° C. and the resulting crystalline solid was collected by filtration to give (1S,6S)-1-phenylmethyl-10-(3-pyridylmethyl)-11-oxo-7-thia-10-azaspiro[5.6]dodecane 7,7-dioxide hydrochloride (8.6 g).
mp: >185° C. (dec.).
IR (Nujol): 1645 cm$^{-1}$.
$[\alpha]_D^{20}$: $-44.4°$ (C=2, DMF).
$^1$H—NMR (CDCl$_3$, $\delta$): 1.0–1.4 (2H, m), 1.5–1.9 (5H, m), 2.0 (2H, m), 2.5 (1H, br t), 3.05 (2H, m), 3.5 (2H, m), 3.9 (1H, d), 4.1–4.4 (2H, m), 4.75 (1H, d), 5.3 (1H, d), 7.1–7.4 (5H, m), 7.9 (1H, dd), 8.5 (1H, d), 8.7 (1H, d), 9.5 (1H, s).

PREPARATION 2

(1) Cyclohexanone (196.3 g) and pyrrolidine (214 g) in benzene (500 ml) were refluxed under nitrogen with a Dean-Stark apparatus, until no more water separated out. The solvents were then evaporated off under nitrogen, and the residual oil was distilled to give 1-(1-pyrrolidinyl)cyclohexene (290 g).
bp: 96°–100° C./10 mmHg.

(2) A mixture of 1-(1-pyrrolidinyl)cyclohexane (85.4 g) and benzyl chloride (100 ml) in dioxane (400 ml) was heated under reflux for 23 hours under nitrogen. Water (100 ml) was then added and the brown oil was distilled to give (2RS)-2-phenylmethylcyclohexanone (47.1 g).
bp: 115°–120° C./3 mmHg.

(3) To a suspension of sodium hydride (1.9 g, 60% dispersion in mineral oil) in toluene (50 ml) was added dropwise triethyl phosphonoacetate (10.3 ml) at 30°–35° C. under nitrogen atmosphere. The mixture was stirred for 1 hour at room temperature. To this nearly clear solution was added dropwise (2RS)-2-phenylmethylcyclohexanone (10.0 g) in toluene (10 ml) at room temperature and the mixture was stirred at 60° C. for 2 hours. After cooling at 0° C., the mixture was washed with 1N hydrochloric acid (50 ml), water (50 ml), saturated aqueous sodium bicarbonate (50 ml) and brine (50 ml). The organic layer was dried over anhydrous magnesium sulfate and concentrated in vacuo. The residue was dissolved in methanol (30 ml) and 5N aqueous potassium hydroxide (30 ml) and refluxed for 2 hours. The mixture was concentrated to half volume in vacuo and acidified (pH=3) with concentrated hydrochloric acid. The mixture was extracted with ethyl acetate-diisopropyl ether (1:1, 500 ml) and the organic layer was extracted with 1N aqueous sodium hydroxide 25 ml×2). The aqueous layer was acidified (pH=3) with concentrated hydrochloric acid and extracted with ethyl acetate-diisopropyl ether (1:1, 50 ml), and the extract was dried over anhydrous magnesium sulfate and concentrated in vacuo. The residue was triturated with hexane to give (2RS)-2-phenylmethyl-1-carboxymethylenecyclohexane (12.3 g).
mp: 98°–100° C.

PREPARATION 3

The following compounds were obtained according to similar manners to those of preparations 1 and 2.

(1) (2R)-2-Phenylmethyl-1-carboxymethylenecyclohexane
mp: 105°–107° C.

(2) (2RS)-2-(4-Methylphenylmethyl)-1-carboxymethylenecyclohexane
mp: 107°–109° C.

(3) (2RS)-2-(4-Chlorophenylmethyl)-1-carboxymethylenecyclohexane
mp: 125°–128° C.

(4) (2RS)-2-(4-Methoxyphenylmethyl)-1-carboxymethylenecyclohexane (5) (2RS)-2-(2-Bromophenylmethyl)-1-carboxymethylenecyclohexane
mp: 144°–145° C.

(6) (2S)-2-(3-Chlorophenylmethyl)-1-carboxymethylenecyclohexane (7) (2RS)-2-(3-Chlorophenylmethyl)-1-carboxymethylenecyclohexane
mp: 105°–113° C.

(8) (2RS)-2-(2-Methylphenylmethyl)-1-carboxymethylenecyclohexane
mp: 140°–141° C.

(9) (2RS)-2-(2,6-Dichlorophenylmethyl)-1-carboxymethylenecyclohexane
mp: 163°–165° C.

(10) (2RS)-2-(2-Chlorophenylmethyl)-1-carboxymethylenecyclohexane
mp: 116°–118° C.

(11) (2RS)-2-(2-Fluorophenylmethyl)-1-carboxymethylenecyclohexane
mp: 82°–84° C.

(12) (2RS)-2-(3-Fluorophenylmethyl)-1-carboxymethylenecyclohexane
mp: 99°–101° C.

(13) (2RS)-2-(1-Naphthylmethyl)-1-carboxymethylenecyclohexane
mp: 154°–155° C.

EXAMPLE 13

The following compound was obtained according to a similar manner to that of Example 5(1).

(1S,6S)-1-Phenylmethyl-10-(3-pyridylmethyl)-11-oxo-7-thia-10-azaspiro[5.6]dodecane 7,7-dioxide hydrochloride
IR (Nujol): 1645 cm$^{-1}$.
$[\alpha]_D^{20}$: −44.4° (C=2, DMF).

EXAMPLE 14

The following compounds were obtained according to a similar manner to that of Example 3(1).

(1) (1S,6S)-1-Phenylmethyl-10-(3-pyridylmethyl)-11-oxo-7-thia-10-azaspiro[5.6]dodecane 7,7-dioxide
IR (Nujol): 1640 cm$^{-1}$.
$[\alpha]_D$= −28.9° (C=1.14, CH$_3$OH).

(2) (1S,6S)-1-Phenylmethyl-10-(3-pyridylmethyl)-11-oxo-7-thia-10-azaspiro[5.6]dodecane 7,7-dioxide hydrochloride
IR (Nujol): 1645 cm$^{-1}$.
$[\alpha]_D^{20}$= −44.4° (C=2, DMF).

What we claim is:

1. A compound of the formula:

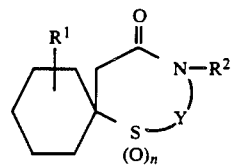

wherein

R$^1$ is ar(lower)alkyl which may have suitable substituent(s),

R$^2$ is hydrogen, lower alkyl which may have suitable substituent(s), or a group of the formula:

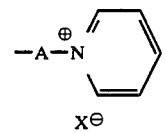

in which A is lower alkylene and X is halogen, n is 0, 1 or 2 and Y is —CH$_2$—CH$_2$— or

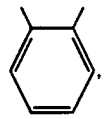

or a pharmaceutically acceptable salt thereof.

2. A compound of claim 1, wherein

R$^1$ is ar(lower)alkyl which may have one to three substituent(s), in which the aryl moiety is selected from the group consisting of phenyl and naphthyl and the substituent is selected from the group consisting of halogen, lower alkoxy and lower alkyl, and R$^2$ is hydrogen; lower alkyl which may have one to three substituent(s) selected from the group consisting of di(lower)alkylamino, halogen and heterocyclic group, in which the heterocyclic group may have one to three substituent(s) selected from the group consisting of halogen, lower alkoxy and lower alkyl; or a group of the formula:

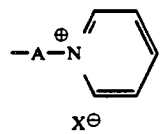

in which A is lower alkylene and X is halogen.

3. A compound of claim 2, wherein

R$^2$ is hydrogen; lower alkyl which may have one to three substituent(s) selected from the group consisting of di(lower)alkylamino, halogen and heterocyclic group, in which the heterocyclic group is selected from the group consisting of pyridyl, morpholinyl, thiazolyl, quinolyl and quinoxalinyl and may have one to three substituent(s) selected from the group consisting of halogen, lower alkoxy and lower alkyl; or a group of the formula:

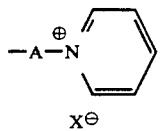

in which A is lower alkylene and X is halogen.

4. A compound of claim 3, wherein
 $R^1$ is ar($C_1$-$C_3$)alkyl which may have one to three substituent(s), in which the aryl moiety is selected from the group consisting of phenyl and naphthyl and the substituent is selected from the group consisting of halogen, lower alkoxy and lower alkyl,
 $R^2$ is hydrogen; $C_1$-$C_4$ alkyl which may have one to three substituent(s) selected from the group consisting of di(lower)alkylamino, halogen and heterocyclic group, in which the heterocyclic group is selected from the group consisting of pyridyl, morpholinyl, thiazolyl, quinolyl and quinoxalinyl and may have one to three substituent(s) selected from the group consisting of halogen, lower alkoxy and lower alkyl; or a group of the formula:

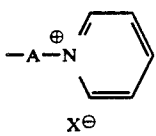

in which A is $C_1$-$C_4$ alkylene and X is halogen.

5. A compound of claim 4, wherein
 $R^1$ ar($C_1$-$C_3$)alkyl which may have one to three substituent(s), in which the aryl moiety is selected from the group consisting of phenyl and naphthyl and the substituent is selected from the group consisting of halogen, $C_1$-$C_3$ alkoxy and $C_1$-$C_3$ alkyl, and
 $R^2$ is hydrogen; $C_1$-$C_4$ alkyl which may have one to three substituent(s) selected from the group consisting of di($C_1$-$C_3$)alkylamino, halogen and heterocyclic group, in which the heterocyclic group is selected from the group consisting of pyridyl, morpholinyl, thiazolyl, quinolyl and quinoxalinyl and may have one to three substituent(s) selected from the group consisting of halogen, $C_1$-$C_3$ alkoxy and $C_1$-$C_3$ alkyl; or a group of the formula:

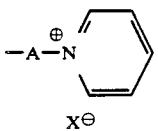

in which A is $C_1$-$C_4$ alkylene and X is halogen.

6. A compound of claim 5, wherein
 $R^1$ is ar($C_1$-$C_3$)alkyl which may have one or two substituent(s), in which the aryl moiety is selected from the group consisting of phenyl and naphthyl and the substituent is selected from the group consisting of halogen, $C_1$-$C_3$ alkoxy and $C_1$-$C_3$ alkyl, and
 $R^2$ is hydrogen; $C_1$-$C_4$ alkyl which may have one to three substituent(s) selected from the group consisting of di($C_1$-$C_3$)alkylamino, halogen and heterocyclic group, in which the heterocyclic group is selected from the group consisting of pyridyl, morpholinyl, thiazolyl, quinolyl and quinoxalinyl and may have one or two substituent(s) selected from the group consisting of halogen, $C_1$-$C_3$ alkoxy and $C_1$-$C_3$ alkyl; or a group of the formula:

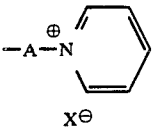

in which A is $C_1$-$C_4$ alkylene and X is halogen.

7. A compound of claim 6, wherein
 $R^1$ is phenyl($C_1$-$C_3$)alkyl,
 $R^2$ is pyridyl($C_1$-$C_3$)alkyl,
 n is 2, and
 Y is —$CH_2CH_2$—.

8. A compound of claim 7, which is (1S,6S)-1-phenylmethyl-10-(3-pyridylmethyl)-11-oxo-7-thia-10-azaspiro[5.6]dodecane 7,7-dioxide or its hydrochloride.

9. A PAF antagonist pharmaceutical composition which comprises, as an active ingredient, an effective amount of a compound of claim 1 or a pharmaceutically acceptable salt thereof in admixture with a pharmaceutically acceptable carriers.

10. A method for treating or preventing PAF-mediated diseases which comprises administering an effective amount of a compound of claim 1 or a pharmaceutically acceptable salt thereof to a human or animal.

* * * * *